(12) United States Patent
Marsland et al.

(10) Patent No.: US 11,911,346 B2
(45) Date of Patent: Feb. 27, 2024

(54) ORALLY ADMINISTRATED THERAPEUTIC FOR TREATING MILD COGNITIVE IMPAIRMENT (MCI) AND IMPROVING HUMAN COGNITIVE FUNCTION

(71) Applicant: BrainCare LLC, Reno, NV (US)

(72) Inventors: Charles H. Marsland, Windermere, FL (US); Stacey Bell, Reno, NV (US)

(73) Assignee: Nutrient Survival LLC, Reno, NV (US)

( * ) Notice: Subject to any disclaimer, the term of this patent is extended or adjusted under 35 U.S.C. 154(b) by 188 days.

(21) Appl. No.: 17/459,889

(22) Filed: Aug. 27, 2021

(65) Prior Publication Data
US 2023/0083707 A1   Mar. 16, 2023

(51) Int. Cl.
*A61K 31/015* (2006.01)
*A61K 9/00* (2006.01)
*A61P 25/28* (2006.01)

(52) U.S. Cl.
CPC .......... *A61K 31/015* (2013.01); *A61K 9/0053* (2013.01); *A61P 25/28* (2018.01)

(58) Field of Classification Search
CPC .................................................. A61K 31/015
See application file for complete search history.

(56) References Cited

U.S. PATENT DOCUMENTS

2010/0074976 A1   3/2010   Fowler et al.

FOREIGN PATENT DOCUMENTS

| WO | 2018/222923 A1 | 12/2018 |
| WO | 2021/127749 A1 | 7/2021 |

OTHER PUBLICATIONS

Cheng et al. Pharmacology, (2014)94(1) pp. 1-12.*
Cheng, Y. et al., "β-Caryophyllene Ameliorates the Alzheimer-Like Phenotype in APP/PS1 Miche through CB2 Receptor Activation and the PPARy Pathway," Pharmacology, vol. 94, pp. 1-12, Aug. 26, 2014.
International Search Report and Written Opinion, dated Nov. 8, 2022, in companion PCT/US2022/41656 application, filed Aug. 26, 2022.

* cited by examiner

*Primary Examiner* — Paul V Ward
(74) *Attorney, Agent, or Firm* — Prince Lobel Tye LLP

(57) ABSTRACT

A therapeutic method of treating mild cognitive impairment and improving human cognitive function, comprising: orally administering Beta-Caryophyllene (BCP), whereas the BCP improves cognitive function.

13 Claims, No Drawings

ORALLY ADMINISTRATED THERAPEUTIC FOR TREATING MILD COGNITIVE IMPAIRMENT (MCI) AND IMPROVING HUMAN COGNITIVE FUNCTION

BACKGROUND

This disclosure relates to oral treatment of mild cognitive impairment and subjective cognitive decline (SCD).

Impaired cognition, and in particular, Alzheimer's disease used to be characterized by two core pathologies: formation of beta-amyloid plaque and neurofibrillary tangles. More recently, neuroinflammation has been added to the mix, and it is known to play a role in the development of the overall pathology including cognitive impairment and decline. Since systemic inflammation is also associated with cognitive impairment and decline, inflammation of the brain and periphery are potential targets for anti-inflammatory drugs to treat or slow the progression of neurological disease.

Because brain inflammation is an important MCI and dementia risk factor, much of the focus today is on the microglial cells, which were only characterized in the mid-1980s. These cells are considered to be the brain's macrophages and are able to secrete both pro- and anti-inflammatory mediators such that it is crucial to maintain homeostatic mechanisms that tip microglia function to the healthy side.

Growing scientific interest has turned to compounds including beta-caryophyllene (BCP), a natural, bicyclic sesquiterpene found in many plants (e.g., oregano, cinnamon, clove, rosemary, wild sage, thyme, and black pepper). Beta-caryophyllene can cross the blood-brain barrier and thus act on the central nervous system. It is an endocannabinoid that activates and selectively binds to the cannabinoid receptor 2 (CB2R), which is mainly localized in the microglial cells.

Activation of CB2R is implicated in the reduction of pro-inflammatory cytokines, and subsequent neuro-inflammation (e.g., lower amounts of IL-1 beta, IL-6, IL-8, and TNF-alpha). Endocannabinoids like BCP exert their anti-inflammatory properties, at least in part, by the activation of the peroxisome proliferator-activated receptor-gamma (PPAR-gamma) pathway. PPAR-gamma is a member of the superfamily of nuclear receptors and has important anti-inflammatory activity, because it inhibits the activation of nuclear factor-kappa beta and the expression of the proinflammatory cytokines, IL-1-beta and TNF-alpha. Activation of CB2R can trigger phagocytosis of beta-amyloid in human macrophages like the microglial cells but not the astrocytoma cells.

Specific Actions of beta-caryophyllene (BCP)

It is likely that BCP protects the brain and body based on its anti-inflammatory/anti-oxidant properties. Transgenic mice mimicking Alzheimer's disease experienced reduced inflammation that prevented cognitive decline after oral ingestion of BCP. BCP has been shown to improve conditions related to its anti-inflammation property: inflammatory bowel disease, pain and inflammation in a neuropathic pain model, and oxidative stress reduction in the glial cells. BCP has also shown promise for treating anxiety and depression, being a plausible therapeutic in diabetes and associated complications, preventing and ameliorating non-alcoholic fatty liver disease, lessening acute and chronic pain, and having an anti-convulsive effect against seizures. In addition, BCP may offer benefit to promote weight loss and reduce cardiovascular disease. In an animal model, BCP was able to decrease the visceral fat index, total and LDL cholesterol, very low-density lipoprotein (VLDL), and pro-inflammatory cytokines. These effects were reversed by treatment with CB2 cannabinoid receptors and PPAR-antagonists, suggesting that BCP activity is mediated by direct binding to CB2 receptors and by the activation of PPAR-agonists.

One clinical study showed that BCP from black pepper mitigates pain. Of the 31 participants, half complained of either acute or chronic pain at the onset of the study. Each received 60 mg of BCP daily for eight weeks. By day 4, 60% reported mitigation of pain and the benefits lasted for one week. About one-third of the participants stated that the level of reduced pain was comparable to non-steroidal anti-inflammatory drugs (NSAIDs) that were used previously. Another group explored the effect of BCP on testosterone levels in women who complained of low libido. The women had an olfactory exposure treatment of a control (glycerol) followed by 3% BCP, each over 20 minutes. Salivary testosterone increased without changing estrogen for the BCP treatment compared to the control period. These findings suggest that BCP may be a remedy with few side effects for women with decreased libido.

It is possible that activation of CB2R from orally consumed BCP may lead to beneficial cognitive effects by reducing the neuroinflammatory response. More involved dietary plans like the Mediterranean and MIND diets have been shown to reduce the risk of cognitive impairment. Both diet plans include mostly fresh foods like fruits, vegetables, whole grains, healthy oils like olive oil, legumes, and seeds and nuts, which are not foods typically consumed by most Americans.

A purpose of the present 8-week, randomized, prospective study is to evaluate the effect of two different doses of BPC on cognition in an elderly population, who have not been diagnosed with mild cognitive impairment or dementia, yet have noticed poorer cognition themselves.

SUMMARY

Mild Cognitive Impairment (MCI) is the stage between the expected cognitive decline of normal aging and the more serious decline of dementia. It's characterized by problems with memory, language, thinking or judgment.

Individuals who have mild cognitive impairment may be aware their memory or mental function has "slipped." This term is referred to as Subjective Cognitive Decline. Family and friends may also notice change, but those changes aren't severe enough to significantly interfere with daily life and or usual activities. Mild Cognitive Impairment may increase the risk of developing dementia or other neurological conditions but some may never get worse and few get better.

Neuroinflammation is known to play a neuropathological role in MCI as well as other forms of cognitive decline. The issue is there are no known therapeutics for these diseases and or neuroinflammation, until now.

As part of the search for affordable non-invasive brain care therapies, our effort to develop novel therapeutics turned toward the natural compound Beta-caryophyllene (BCP which is found in many plants including clove, black pepper and basil). It is a commercially available purified compound that is scientifically known to cross the blood-brain barrier. Until now, its primary use has been as an essential oil and or as a compound used for sore joints and or aches associated with influenza. Our work focused on the use of the compound, in a purified format delivered orally, targeted the reduction of microglial cell based neuro-inflammation.

In order to determine the effectiveness, several oral delivery forms of BCP were developed as well as a randomized study, disclosed herein, established to determine the effect of BCP on cognitive function in individuals who have noticed worsening of memory. In our 8-week study, 52 participants were randomized to two different doses of BCP: 90 mg (n=29) or 180 mg (n=29). At baseline, week 4, and week 8, cognitive function was assessed using the Cognitive Failures Questionnaire (CFQ) and Cambridge Brain Sciences (CBS) tests; both were taken online. At baseline, the average age was 67±5 years.

For each of the four CFQ sub-scale scores, all measurements at week 4 and week 8 improved for both groups (i.e., one or two BCP capsules). Taking two BCP capsules resulted in significant improvement for all four sub-scale scores at week 4 and week 8 compared to baseline. In contrast, those taking one BCP capsule had a significant improvement yet only three times. The percentage improvement in the sub-scale scores for those taking two BCP capsules were about twice greater than experienced by those taking one BCP capsule.

Baseline mean CBS brain scores for the four tests were near or below average; the percentage changes for all scores were small (2-5% increases, except for two tests for those taking two BCP capsules, which had increases of 7% for Spatial Planning and 10% for Double Trouble). The percentage of participants who improved in all tests over 8 weeks was between 40% and 73%; similar improvements were observed between those taking one BCP capsule or two capsules. Over 8 weeks, the biggest improvements were observed for the combined summed means of all four tests for those with baseline mean scores at or below 100 (those taking one BCP capsule improved 5.0±9.8%, and those taking two capsules improved 9.0±12.9%).

Compliance with the BCP capsules was excellent and no other dietary or lifestyle changes were imposed. As no therapeutic treatments are available to treat Mild Cognitive Impairment (MCI) and/or dementia, the current study suggests that the oral use of 180 mg of BCP is an effective way to treat MCI and improve cognitive function in an elderly population.

All examples and features mentioned below can be combined in any technically possible way.

In one aspect, a method of improving human cognitive function comprises orally administering Beta-Caryophyllene (BCP), whereas the BCP improves cognitive function. In some regards this improvement is at least about 8%. In some examples the BCP is administered in a dose of at least about 90 mg daily. In an example the administration of a dose of at least about 90 mg BCP daily continued for a plurality of weeks. In an example the administration of a dose of at least about 90 mg BCP daily continued for up to eight weeks. In an example the BCP is administered in a dose of at least about 180 mg daily. In an example the BCP improves cognitive function by up to about 63%. In an example the BCP is derived from at least one of oregano, cinnamon, clove, rosemary, wild sage, thyme, and black pepper. In an example the administration of BCP is conducted daily. In an example cognitive function was measured after four weeks and eight weeks of daily BCP administration. In an example cognitive function improved by all measures after four weeks of daily BCP administration. In an example cognitive function improved by all measures after eight weeks of daily BCP administration as compared to four weeks of daily BCP administration.

DETAILED DESCRIPTION

Examples of the systems, methods and apparatuses discussed herein are not limited in application to the details of construction and the arrangement of components set forth in the following description or illustrated in the accompanying drawings. The systems, methods and apparatuses are capable of implementation in other examples and of being practiced or of being carried out in various ways. Examples of specific implementations are provided herein for illustrative purposes only and are not intended to be limiting. In particular, functions, components, elements, and features discussed in connection with any one or more examples are not intended to be excluded from a similar role in any other examples.

Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

Also, the phraseology and terminology used herein is for the purpose of description and should not be regarded as limiting. Any references to examples, components, elements, acts, or functions of the computer program products, systems and methods herein referred to in the singular may also embrace embodiments including a plurality, and any references in plural to any example, component, element, act, or function herein may also embrace examples including only a singularity. Accordingly, references in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or"

METHODS

Eighty subjects were recruited by a third party with the anticipation of having 60 complete the study. Fifty-nine enrolled in the study with seven later withdrawing. Participants, who meet the entry criteria, were randomized to one or two servings of BCP daily and asked to complete baseline and weekly data collection forms, which were sent electronically (e.g., anthropometry, cognitive testing, quality of life). All signed a consent form which abided by the *Helsinki Declaration,* seventh revision. The study lasted eight weeks.

Entry Criteria and Recruitment

The entry criteria were to be aged 60-80 years, worried about their own brain function (e.g., losing memory, concentration, focus; and referred to as Subjective Cognitive Decline), and being overweight or obese according to body mass index (BMI; 25-40 kg/m$^2$). Each candidate needed to own a computer and be versatile on its use in order to complete weekly data collection forms and perform online brain games. Participants could not have been diagnosed with Alzheimer's disease, Parkinson's disease, mild cognitive impairment, or any other neurodegenerative condition, but could have other chronic conditions, as long as they were well controlled. No one with COVID-19 was admitted to the study, and throughout the 8 weeks, if anyone contracted the coronavirus, they were excluded from the study. Candidates had to be naive to using supplements of beta-caryophyllene (BCP).

The participants were screened and recruited by the third party, who then remained in regular contact with them to assure weekly compliance with requested data. If more than one questionnaire was submitted, the last one was used. Participants were compensated $100 upon submission of all data at week 8.

Cognitive Testing Using the Cognitive Failures Questionnaire (CFQ)

The CFQ (available from the University of California, Berkeley) probes minor mistakes that most people make occasionally but sometimes they happen more frequently. The 25-question survey was developed to assess the frequency that individuals experience these mistakes in cognitive function, such as absent-mindedness, in everyday life — slips and errors of perception, memory, and motor functioning. The CFQ scoring system used for each question was: 0=Never; 1=Very rarely; 2=Occasionally; 3=Quite often; 4=Very often. Four summed sub-scale scores with similar attributes were also determined for a Total CFQ score; Forgetfulness (a tendency to forget something that is known or planned, for example, names, intentions, appointments, and words); Distractibility (mainly in social situations such as being absentminded or easily disturbed with one person or in a group); and False triggering (interrupted ability to pay attention leading to making errors in thinking and acting logically).

The CFQ cognitive test was sent to the participants electronically at baseline, week 4, and week 8. A lower score indicated better cognitive function.

Cognitive Testing Using Cambridge Brain Sciences (CBS), Toronto, Canada

The Cambridge Brain Sciences (CBS) included a battery of four tests to measure various aspects of cognition and that affected different regions of the brain. Normal scores for each test ranged from 87 to 113. Improvement meant that the mean score increased from baseline to week 8, no change meant that the score at week 8 was the same as baseline, and worse indicated that the score at week 8 was lower than at baseline.

The first test is the Spatial Planning test, which addresses reasoning and planning. It tests for non-Alzheimer's dementia but has a high correlation with aging. It has a high reproducibility and is useful to distinguish impaired and unimpaired populations. The parts of the brain implicated include: frontal lobe, mid-dorsolateral frontal cortex, caudate nucleus, thalamus, lateral premotor, and anterior cingulate.

The second test is Double Trouble and addresses concentration and response inhibition. It can detect early Alzheimer's disease and age-related cognitive decline. It has a high reproducibility and is useful in distinguishing impaired and unimpaired aging. The parts of the brain involved include the right prefrontal cortex and dorsolateral region.

The third test is the Monkey Ladder, which relates visuospatial and working memory. The test can detect early Alzheimer's disease, non-Alzheimer's dementia, and age-related cognitive decline. The parts of the brain involved included: the mid-dorsolateral prefrontal cortex, premotor cortex, and posterior parietal cortex.

The fourth test is the Feature Match (aka Feature Selection), which addresses concentration and attention, and correlates well with aging. It can detect early Alzheimer's disease, and non-Alzheimer's dementia. The parts of the brain involved include the mid-ventrolateral frontal cortex and the right inferior frontal gyms.

Nutrition Intervention

Clove oil, (Syzygium aromaticum, served as the source of BCP. Capsules for the study were prepared by a third party. Each capsule contained 100 mg of clove oil containing 90% BCP and 350 mg of rice bran oil. The group taking one capsule daily received 90 mg of BCP and the group taking two capsules received 180 mg. Each capsule had a screw-off top. Participants were told to empty the contents of the capsule into the mouth and leave it under the tongue for a couple of minutes before swallowing. Everyone was told to take the one or two capsules in the morning. Capsules were provided at no charge to the participants.

Statistics

An independent consultant analyzed the data. Anthropometric data (height and weight) obtained from the recruiting company were not used in the analyses. Instead baseline data obtained when the study was about to start were used because these more closely aligned with subsequent, weekly body weight data provided by the participants.

Subjects were initially randomized to take one or two BCP-containing capsules daily and were evenly matched by: gender, body weight (body mass index≥30 $kg/m^2$ or less than 30 $kg/m^2$), and age (60 to less than 70 years old, and 70 years and older). At week 4, four subjects were removed from the study due to the lack of BCP capsules. Two subjects were randomly removed from each group (2/28 in the two capsule/day group; 2/29 in the one capsule/day group). Random numbers were generated between 1 and 28 for the two/day group, which were then sorted by highest to lowest. The first two subjects were removed. The same randomization was performed to remove two subjects in the one capsule/day group. The randomization procedures for removal of subjects were performed by someone not involved in the study.

The data are presented as mean±standard deviation (S.D.) at baseline, week 4, and week 8. Results from the Cognitive Failures Questionnaire and Cambridge Brain Sciences are compared using the Student's t-test in each intervention group between baseline and week 4 and between baseline and week 8. Significance was defined as p≤0.05. At each time point, the percentage change was compared with the values at baseline. This calculation was only obtained from the means between each time point, and the statistical analysis was not made on these percentage changes.

For Cambridge Brain Sciences tests, some responses were flagged as being a highly unusual response (found in less than 1% of Cambridge Brain Sciences normative database). It may be that the participant did not understand the instructions for the test or was distracted. These scores were considered to be invalid and excluded from the final analysis. For each participant, the combined mean scores of all four CBS tests were summed for at baseline and at week 8. The participants were then grouped according to these mean baseline score of all four tests as: below average (less than or equal to 100) and average and above (greater than 100).

RESULTS

Fifty-nine subjects entered the study with an average age of 67±5 years. Females comprised 58% of the group. The mean body weight was 88±15 kg and body mass indexes (BMIs) showed that 2% were normal weight, 36% were overweight, and 62% obese.

Seven subjects withdrew. Four were randomly selected before week 4 to be withdrawn due to lack of capsules; two were removed from each dietary intervention group. Three others withdrew; one at baseline who didn't like the study (taking one capsule per day), another withdrew after week 2 because they wanted more compensation (taking two capsules daily), and the third person withdrew after completing week 5 because they didn't like taking the capsules (taking one capsule daily). The final number of subjects to complete the study was 52 subjects (88% retention), leaving each dietary intervention group with 26 subjects.

At baseline, subjects were fairly well matched between the groups for age, gender, and BMI (Table 1). There were more women in the one capsule per day group compared to those taking two (62% female vs. 55% female). The mean BMI was similar between the groups: 32±6 kg/m$^2$ in the one capsule per day group and 32±5 kg/m$^2$ in the two capsule per day group. More participants in the two BCP capsules daily had Class 1 Obesity (48% vs. 34% in the one capsule daily group). However, those in the one BCP capsule daily included more participants in the Class 2 Obesity group (24% vs. 7% in the two capsule per day group). None of the participants were told by their physician to follow a special diet to maintain or improve brain function.

Participants in both groups had 100% compliance with the dietary interventions over the 8-week study. Participants remained weight stable, which was the objective of the study so that weight change was not a confounding variable on cognitive changes (data not shown). For those taking one BPC capsule daily baseline was BMI 32±6 kg/m$^2$ and at week 8 it was 31±5 kg/m$^2$. For those taking two capsules daily, baseline BMI was 32±5 kg/m$^2$ and at week 8 it was 32±6 kg/m$^2$.

Cognitive Failures Questionnaire (CFQ)

Four Summed Sub-Scale CFQ Scores

For each of the four sub-scale scores, all measurements at week 4 and week 8 were lower than at baseline for both dietary intervention groups (i.e., one or two BCP capsules), indicating improvement in cognition (Tables 2a-2d). Taking two BCP capsules resulted in significant improvement for all four sub-scale scores at week 4 and week 8 compared to baseline (P≤0.05). Unlike taking two BCP capsules, those taking one BCP capsule only had a significant improvement for Forgetfulness at week 8 compared to baseline (P≤0.05) (Table 2b) and for False Triggering at weeks 4 and 8 compared to baseline (P≤0.05) (Table 2d). The percentage improvement in the sub-scale scores for those taking two BCP capsules were about twice greater than experienced by those taking one BCP capsule (Tables 2a-2d).

The participants taking two BCP capsules experienced significant improvement in the Total CFQ sub-scale scores of 25% and 30% at weeks 4 (P≤0.01) and 8 (P≤0.005), respectively (Table 2a). Those taking one BCP capsule improved 14% at week 4 and 16% at week 8. For the Forgetfulness sub-score, those taking two capsules improved more than those taking one BCP capsules at week 4 (27% vs. 14%) and at week 8 (27% vs. 17%) (Table 2b). Those taking one BCP experienced a significant improvement at week 8 (P≤0.05), and those taking two BCP capsules achieved a significant benefit at both weeks 4 and 8 (P≤0.01) (Table 2b).

For the Distractibility sub-score, the participants taking two BCP capsules improved 20% at week 4 and 29% at week 8 (P≤0.001, respectively), in contrast to non-significant improvements for those taking one BCP capsule of 8% at week 4 and 9% at week 8 (Table 2c). The False Triggering sub-scores improved the most in the group taking two BCP capsules compared to any other sub-score for either of the one and two BCP capsule groups (Table 2d). For those taking one BCP capsule, significant improvement was observed at week 4 (18%, P 0.05) and week 8 (19%, P≤0.05). With the group taking two BCP capsules, a greater improvement was observed at week 4 (33%, P≤0.01) and week 8 (36%, P≤0.01).

Changes in Individual CFQ Questions

Of the 25 questions on the CFQ questionnaire, improvement was observed for nearly all questions over 8 weeks, but only eight achieved significance. In most cases, greater improvement was found in those taking two BCP capsules compared to one; often it was two or three times more.

Changes in CFQ that achieved statistical significance (Table 3a-3h). Eight of the twenty-five CFQ questions improved significantly for both dietary options (one or two BCP capsules) (Tables 3a-3h). Baseline questions were 2.0 or greater for 10 of the 16 options (8 for one BCP capsule and 8 for two BCP capsules), indicating difficulty at baseline in these aspects of cognitive function. Mostly two capsules showed greater improvement than taking one BCP capsule, and no worsening of cognition was observed for either dietary intervention.

The question related to "having to re-read something because you were thinking of something else" significantly improved with two BCP capsules at week 4 (39%) and week 8 (39%) (P≤0.005 for both time points; Table 3a). For both BCP capsule groups, significant benefit was observed in "remembering why you went from one room to another" (Table 3b). For those taking one BCP capsule, significant improvement was observed at week 4 (29%; P≤0.005) and week 8 (29%; P≤0.005) compared to baseline. For those taking two BCP capsules, compared to baseline, improvement was observed at week 4 (39%; P≤0.0005) and week 8 (39%; P≤0.0005).

The score for "remembering whether you turned a light off or locked a door" was significantly improved only for those taking two BCP capsules (Table 3c). Compared to baseline, at week 4 (45% better; P≤0.005) and week 8 (40% better P≤0.005). The "ability to remember where you put a newspaper or book" improved in both BCP groups (Table 3d). For those taking one BCP capsule, the percentage improvement at both weeks 4 and 8 was 22% (P≤0.05) compared to baseline. Those taking two BCP capsules, compared to baseline, improved 19% at week 4 (P≤0.01) and at week 8 improved 29% (P≤0.01).

Accidently "misplacing something like putting fruit in the cupboard and the bowl in the refrigerator" was only significant for those taking two BCP capsules (Table 3e). Compared to baseline, at week 8 there was 63% improvement (P≤0.05). The participants taking two BCP capsules daydreamed significantly less when they were supposed to be listening to something (Table 3f). At both week 4 (28% better; P≤0.05) and week 8 (33%; P≤0.05) improvement occurred compared to baseline.

Becoming less distracted and doing something else unintentionally after starting a task improved significantly for those taking two BCP capsules at weeks 4 and 8 (30%; P≤0.005 for both time points) (Table 3g). The ability to remember things that are on the "tip of the tongue" improved significantly for those taking one BCP capsule at week 8 compared to baseline (19%; P≤0.01) and for those taking two BCP capsules at week 4 compared to baseline (20%; P ≤0.01 (Table 3h).

Changes in CFQ that did not achieve statistical significance (Table 3i). Seventeen of the twenty-five CFQ questions did not achieve significance over the 8-week study for either dietary intervention (Table 3i). Most mean baseline responses (15/17) in both BCP groups have values of 2.0 or less, which indicated that they were near-normal, and, thus, significant improvements would be unlikely. Despite seemingly high percentage improvements (many of 20% to 30%), the large standard deviations made achieving significance less likely.

Individual questions that did not result in significance improvement included: forgetting someone's name, forgetting why entered a store, failing to remember anything to say, forgetting which way to turn on a road, not paying bills, forgetting to look at signposts, confusing left and right when giving directions, bumping into people, not listening when told someone's name, worrying that something said was insulting, failing to hear people when doing something else, losing your temper, forgetting why went into the supermarket, using a word incorrectly, having trouble making up your mind, forgetting an appointment, and dropping things (Table 3i).

The only times that a response was worse at week 4 and 8 than baseline was in those taking one BCP capsule at week 4 and week 8 for confusing left and right when giving others directions; and at week 4 and week 8 for forgetting an appointment (Table 3i). However, none of these were significant.

Cambridge Brain Sciences

Cambridge Brain Sciences Actual Scores and Percentage Change

One BCP capsule. Mean test scores at baseline indicated that the participants were either on the low side of normal which was 87-99 (88±12 Double Trouble and 96±6 Feature Match) or closer to the mid-point of 100 (102±11 Spatial Planning, and 101±6 Monkey Ladder) (Table 4). Considering all the subjects who had a sub-optimal score at baseline (i.e., less than 87), 31% improved during the study to a normal score on any test (i.e., 87 or greater).

Those taking one BCP capsule experienced average improvement for each test between 2% and 5%. For the Double Trouble test, 56% had sub-optimal scores at baseline and by week 8, only 44% had sub-optimal score. No meaningful changes in normalization were observed for the other three tests.

Two BCP capsules. Mean test scores at baseline were similar to those taking one capsule (Table 4). The means of three tests (Spatial Planning, Double Trouble, and Feature Match) were below 100 (96±10, 88±12, and 99±7, respectively). Only the Monkey Ladder baseline mean exceeded 100 (102±6). The biggest improvements in mean test scores that were significant for both (P<0.05) were for Double Trouble (10%) and followed by 7% for Spatial Planning. A smaller increase in mean score between baseline and week 8 was observed for Monkey Ladder (2%), and there was no change in Future Match.

Improvement, Worsening, and No Change in Cambridge Brain Sciences Tests between Baseline and Week 8

The overall percentage of those who improved, worsened, and remained the same for the four tests showed that more than half of all participants improved on each test, except for Feature Match for those taking two BCP capsules (Table 5).

The percentage of those taking one BCP capsule that improved for Spatial Planning was 73%, for Double Trouble was 60%, Monkey Ladder was 70%, and Feature Match was 54%. The percent that had worse scores were 19% for Spatial Planning, 36% for Double Trouble, 26% for Monkey Ladder, and 33% for Feature Match. The remaining percentage of participants had no change.

The percentage of those taking two BCP capsules that improved for Spatial Planning was 72%, Double Trouble was 64%, Monkey Ladder was 68%, and Feature Match was 40% (Table 5). The percentage that had worse scores were 20% for Spatial Planning, 23% for Double Trouble, 4% for Monkey Ladder, and 44% for Feature Match. The remaining percentage of participants had no change.

Summed Combined Means of the Four Cambridge Brain Sciences Test Scores at Baseline and Week 8

The mean combined sum of the four Cambridge Brain Sciences test scores at baseline was below the average of 100 (Table 6). Those taking one BCP capsule had a mean baseline of four test scores of 96.8, which increased to 99.8 at week 8, indicating a 3.6±10.0% increase. For those taking two BCP capsules, mean baseline summed score was 97.2 and increased to 101.0, which was a 4.6±12.1% increase.

Looking at only those with mean combined summed baseline scores for four tests of less than or equal to 100 revealed that those taking one BCP capsule experienced a 5.0±9.8% increase (baseline was 92.3; week 8 was 96.8). Those taking two BCP capsules with baseline mean summed scores of 100 or less, experienced a 9.0%±12.9% increase (baseline was 91.0; week 8 was 98.8). In contrast, those with baseline mean combined summed scores over 100 for the four Cambridge Brain Sciences tests did not change appreciably at week 8 (−0.7±9.4% for those taking one BCP and −1.5%±7.5% for those taking two BCP capsules).

DISCUSSION

Neuroinflammation is an emerging cause of age-related dementia, and the microglial cells are of interest, as they are the resident macrophages in the brain. Cloves contain a rich source of beta-caryophyllene (BCP), which has been shown in animal models to reduce inflammation. Here it was shown that BCP obtained from an extract of cloves improved cognition in an elderly population, who reported being worried about their memory. Both dietary interventions of BCP (90 mg or 180 mg) led to improvement in various aspects of cognition over 8 weeks, but taking two capsules resulted in more improvement. This was the first report to our knowledge where BCP favorably affected cognition.

Based on the results of the Cognitive Failures Questionnaire (CFQ), each of the four sub-scale scores measurements at week 4 and week 8 improved for both dietary intervention groups compared to baseline (i.e., one or two BCP capsules). Taking two BCP capsules resulted in significant improvement for all four sub-scale scores at week 4 and week 8 compared to baseline. In contrast, those taking one BCP capsule had a significant improvement only three of eight times. The percentage improvement in the sub-scale scores for those taking two BCP capsules were about twice greater than experienced by those taking one BCP capsule. Given the dose effects of BCP, it is possible that a larger dose than the ones tested could lead to additional cognitive improvement.

Small benefits were observed when the mean of each for the four Cambridge Brain Sciences tests were looked at individually. Of the eight tests (four tests for each intervention), only two improved more than the anticipated 5% achieved by from learning. More than half (but mostly 60-70%) of the participants improved on the cognitive tests. Only one test, Feature Match, had only 40% of the group improve after consuming two BCP capsules. This was the only test in either dietary intervention where a higher percentage of participants experienced a worse score at week 8 compared to baseline. This test specifically addresses concentration and attention, and correlates well with aging, but other tests measured these same attributes and more improvement was observed.

The participants with lower mean combined summed Cambridge Brain Sciences baseline and week 8 test scores were more likely to improve over 8 weeks. Those taking one BCP capsule improved 5%, which is what would have been expected from taking multiple cognitive tests over a short period of time. The group taking two BCP capsules had nearly double what would be expected (9%) improvement. This finding lends support for 180 mg of BCP to improve cognition in an elderly population, who at the onset of the study, had poor cognition. There were no other obvious changes to the participants during the study; the group was weight stable and reported they were compliant with the dietary interventions.

The limitation of the study was the lack of a placebo group. However, this was a pilot study to determine if the doses selected had any impact on cognition, which they both did. Given the improvement observed between 90 mg and 180 mg of BCP, it seems likely that a placebo group would not promote significant benefit. The participants self-reported that they noticed they had memory difficulties. It would have been preferable to have everyone screened and accrue those with similar levels of mild cognitive impairment.

In summary, there are no treatments for dementia, and use the natural BCP compound is an effective way to improve cognition. The participants found the intervention satisfactory in that compliance was excellent. Results from two different cognitive testing tests improved for both dietary interventions, but better results were observed in those using 180 mg of BCP.

TABLE 1

Baseline comparisons between dietary intervention groups*

| | Group 1 = 29 (one capsule daily) | Group 2 = 29 (two capsules daily) |
|---|---|---|
| Age (years) | 67 ± 5 | 68 ± 4 |
| Gender (% female) | 62 | 55 |
| Body weight (kg) | 90 ± 18 | 88 ± 11 |
| Height (cm) | 66.0 ± 4.7 | 65.0 ± 4.1 |
| BMI (kg/m$^2$) | 32 ± 6 | 32 ± 5 |
| ≤25 | 2 (7%) | 0 (0%) |
| ≤30 | 9 (31%) | 11 (38%) |
| ≤35 Class 1 Obesity+ | 10 (34%) | 14 (48%) |
| ≤40 Class 2 Obesity | 7 (24%) | 2 (7%) |
| >40 Class 3 Obesity | 1 (3%) | 2 (7%) |

*Data presented as mean ± standard deviation

+Based on the following reference: National Heart, Lung, and Blood Institute. Classification of Overweight and Obesity by BMI, Waist Circumference, and Associated Disease Risks Table 2. Changes in four summed sub-scores of the Cognitive Failures Questionnaire (CFQ) (lower scores are better)

TABLE 2a

Changes in Total Summed Sub-score of the Cognitive Failures Questionnaire (CFQ) (lower scores are better)

| Time | Group taking one capsule of beta-caryophyllene (BCP) daily (n = 26) | Group taking two capsules of beta-caryophyllene daily (n = 26) |
|---|---|---|
| Total CFQ | | |
| Baseline | 39 ± 12 | 39 ± 16 |
| Week 4 vs. baseline | 34 ± 10 | 29 ± 14* |
| | 14% better | 25% better |
| Week 8 vs. baseline | 33 ± 11 | 27 ± 11** |
| | 16% better | 30% better |

*P ≤ 0.01 and **P ≤ 0.005 compared to baseline of two BCP capsules, using t-test, respectively TABLE 2b Changes in Forgetfulness Summed Sub-score of the Cognitive Failures Questionnaire (CFQ) (lower scores are better)

| Time | Group taking one capsule of beta-caryophyllene (BCP) daily (n = 26) | Group taking two capsules of beta-caryophyllene daily (n = 26) |
|---|---|---|
| Forgetfulness | | |
| Baseline | 16 ± 5 | 16 ± 6 |
| Week 4 | 14 ± 5 | 12 ± 5^ |
| vs. baseline | 14% better | 27% better |
| Week 8 | 13 ± 5* | 12 ± 5^ |
| vs. baseline | 17% better | 27% better |

*P ≤ 0.05 compared to baseline of one BCP capsule, by t-test
^P ≤ 0.01 compared to baseline of two BCP capsules, by t-test, respectively TABLE 2c Changes in Distractibility Summed Sub-score of the Cognitive Failures Questionnaire (CFQ) (lower scores are better)

| Time | Group taking one capsule of beta-caryophyllene (BCP) daily (n = 26) | Group taking two capsules of beta-caryophyllene daily (n = 26) |
|---|---|---|
| Distractibility | | |
| Baseline | 13 ± 4 | 13 ± 5 |
| Week 4 | 11 ± 4 | 10 ± 5* |
| vs. baseline | 8% better | 20% better |
| Week 8 | 11 ± 3 | 9 ± 4* |
| vs. baseline | 9% better | 29% better |

*P ≤ 0.001 compared to baseline for two BCP capsules, using t-test, respectively

TABLE 2d

Changes in False Triggering Summed Sub-score of the Cognitive Failures Questionnaire (CFQ) (lower scores are better)

| Time | Group taking one capsule of beta-caryophyllene (BCP) daily (n = 26) | Group taking two capsules of beta-caryophyllene daily (n = 26) |
|---|---|---|
| False triggering | | |
| Baseline | 12 ± 4 | 11 ± 6 |
| Week 4 | 9 ± 4* | 7 ± 4^ |
| vs. baseline | 18% better | 33% better |
| Week 8 | 9 ± 4* | 7 ± 4^ |
| vs. baseline | 19% better | 36% better |

*P ≤ 0.05 compared to baseline for one BCP capsule, using t-test
^P ≤ 0.01 compared to baseline for two BCP capsules, using t-test, respectively Table 3. Changes in individual questions from the Cognitive Failures Questionnaire (lower score is better)

TABLE 3a

Do you read something and find you haven't been thinking about it and must read it again?

| Time | Group taking one capsule of beta-caryophyllene (BCP) daily (n = 26) | Group taking two capsules of beta-caryophyllene daily (n = 26) |
|---|---|---|
| Baseline | 1.9 ± 1.2 | 2.3 ± 0.8 |
| Week 4 | 1.7 ± 0.9 | 1.5 ± 0.9* |
| vs. Baseline | 11% better | 39% better |
| Week 8 | 1.6 ± 0.9 | 1.4 ± 0.8* |
| vs. Baseline | 16% better | 39% better |

*P ≤ 0.005 compared to baseline for two capsules, using t-test

TABLE 3b

Do you find you forget why you went from one place of the house to the other?

| Time | Group taking one capsule of beta-caryophyllene (BCP) daily (n = 26) | Group taking two capsules of beta-caryophyllene daily (n = 26) |
|---|---|---|
| Baseline | 2.4 ± 0.9 | 2.3 ± 1.0 |
| Week 4 | 1.7 ± 0.6* | 1.4 ± 0.7^ |
| vs. Baseline | 29% better | 39% better |
| Week 8 | 1.7 ± 0.6* | 1.4 ± 0.8^ |
| vs. Baseline | 29% better | 39% better |

*P ≤ 0.005 compared to baseline for one capsule, using t-test
^P ≤ 0.0005 compared to baseline for two capsules, using t-test

TABLE 3c

Do you find you forget whether you've turned off a light or locked the door?

| Time | Group taking one capsule of beta-caryophyllene (BCP) daily (n = 26) | Group taking two capsules of beta-caryophyllene daily (n = 26) |
|---|---|---|
| Baseline | 1.8 ± 1.0 | 2.0 ± 1.0 |
| Week 4 | 1.6 ± 0.8 | 1.1 ± 0.9* |
| vs. Baseline | 11% better | 45% better |
| Week 8 | 1.5 ± 0.7 | 1.2 ± 0.7* |
| vs. Baseline | 17% better | 40% better |

*P ≤ 0.005 compared to baseline for two BCP capsules, using t-test

TABLE 3d

Do you forget where you put something like a newspaper or a book?

| Time | Group taking one capsule of beta-caryophyllene (BCP) daily (n = 26) | Group taking two capsules of beta-caryophyllene daily (n = 26) |
|---|---|---|
| Baseline | 2.3 ± 0.9 | 2.1 ± 1.2 |
| Week 4 | 1.8 ± 0.9* | 1.7 ± 0.9^ |
| vs. Baseline | 22% better | 19% better |
| Week 8 | 1.8 ± 0.7* | 1.5 ± 0.9^ |
| vs. Baseline | 22% better | 29% better |

*P ≤ 0.05 compared to baseline for one BCP capsule, using t-test
^P ≤ 0.01 compared to baseline for two BCP capsules, using t-test

TABLE 3e

Do you find you accidentally misplace things like placing the fruit in the cupboard and the bowl in the refrigerator?

| Time | Group taking one capsule of beta-caryophyllene (BCP) daily (n = 26) | Group taking two capsules of beta-caryophyllene daily (n = 26)* |
|---|---|---|
| Baseline | 1.2 ± 0.9 | 0.8 ± 1.0 |
| Week 4 | 1.0 ± 0.8 | 0.7 ± 0.9 |
| vs. Baseline | 17% better | 13% better |
| Week 8 | 0.9 ± 0.7 | 0.3 ± 0.5* |
| vs. Baseline | 25% better | 63% better |

*P ≤ 0.05 compared to baseline for two BCP capsules, using t-test

TABLE 3f

Do you daydream when you ought to be listening to something?

| Time | Group taking one capsule of beta-caryophyllene (BCP) daily (n = 26) | Group taking two capsules of beta-caryophyllene daily (n = 26) |
|---|---|---|
| Baseline | 1.9 ± 0.8 | 1.8 ± 1.1 |
| Week 4 | 1.6 ± 0.8 | 1.3 ± 0.9* |
| vs. Baseline | 16% better | 28% better |
| Week 8 | 1.7 ± 0.9 | 1.2 ± 0.9* |
| vs. Baseline | 11% better | 33% better |

*P ≤ 0.05 compared to baseline for two BCP capsules, using t-test, respectively

TABLE 3g

Do you start doing one thing at home and get distracted and do something else (unintentionally)?

| Time | Group taking one capsule of beta-caryophyllene (BCP) daily (n = 26) | Group taking two capsules of beta-caryophyllene daily (n = 26) |
|---|---|---|
| Baseline | 2.3 ± 0.8 | 2.7 ± 1.0 |
| Week 4 | 2.3 ± 0.8 | 1.9 ± 0.8* |
| vs. Baseline | no change | 30% better |
| Week 8 | 2.2 ± 0.6 | 1.9 ± 0.7* |
| vs. Baseline | 4% better | 30% better |

*P ≤ 0.005 compared to baseline for two BCP capsules, using t-test, respectively

TABLE 3h

Do you find you can't quite remember something although it's "on the tip of your tongue"?

| Time | Group taking one capsule of beta-caryophyllene (BCP) daily (n = 26) | Group taking two capsules of beta-caryophyllene daily (n = 26) |
|---|---|---|
| Baseline | 2.6 ± 0.8 | 2.5 ± 0.9 |
| Week 4 | 2.3 ± 0.8 | 2.0 ± 1.0^ |
| vs. Baseline | 12% better | 20% better |
| Week 8 | 2.1 ± 0.7* | 2.2 ± 0.8 |
| vs. Baseline | 19% better | 12% better |

*P ≤ 0.01 compared to baseline for one BCP capsule, using t-test
^P ≤ 0.01 compared to baseline for two BCP capsules, using t-test

TABLE 3i

Non-significant changes in responses to CFQ

| Time | Group taking one capsule of beta-caryophyllene (BCP) daily (n = 26) | Group taking two capsules of beta-caryophyllene daily (n = 26) |
|---|---|---|
| Do you find you forget people's names? | | |
| Baseline | 2.5 ± 0.9 | 2.5 ± 0.9 |
| Week 4 | 2.2 ± 1.0 | 2.0 ± 0.9 |
| vs. Baseline | 12% better | 20% better |
| Week 8 | 2.2 ± 0.8 | 2.0 ± 1.0 |
| vs. Baseline | 12% better | 20% better |
| Do you find you forget what you came to the store to buy? | | |
| Baseline | 1.7 ± 1.1 | 1.5 ± 0.9 |
| Week 4 | 1.5 ± 0.8 | 1.0 ± 0.9 |
| vs. Baseline | 12% better | 33% better |
| Week 8 | 1.4 ± 0.8 | 1.1 ± 0.9 |
| vs. Baseline | 18% better | 27% better |
| Do you find you can't think of anything to say? | | |
| Baseline | 1.3 ± 0.7 | 1.1 ± 0.9 |
| Week 4 | 1.1 ± 0.8 | 0.8 ± 0.8 |
| vs. Baseline | 15% better | 27% better |
| Week 8 | 1.3 ± 0.8 | 0.8 ± 0.7 |
| vs. Baseline | no change | 27% better |
| Do you find you forget which way to turn on a road you know well but rarely use? | | |
| Baseline | 1.1 ± 0.8 | 0.9 ± 0.8 |
| Week 4 | 0.8 ± 0.7 | 0.6 ± 0.8 |
| vs. Baseline | 27% better | 33% better |
| Week 8 | 0.8 ± 0.7 | 0.5 ± 0.6 |
| vs. Baseline | 27% better | 44% better |
| Do you lose track of paying bills? | | |
| Baseline | 1.3 ± 0.9 | 1.0 ± 0.9 |
| Week 4 | 1.0 ± 0.8 | 0.9 ± 1.0 |
| vs. Baseline | 23% better | 10% better |
| Week 8 | 1.1 ± 0.8 | 0.7 ± 0.9 |
| vs. Baseline | 15% better | 30% better |
| Do you fail to notice signposts on the road? | | |
| Baseline | 1.2 ± 0.8 | 1.0 ± 0.8 |
| Week 4 | 1.0 ± 0.7 | 0.7 ± 0.7 |
| vs. Baseline | 17% better | 30% better |
| Week 8 | 1.0 ± 0.8 | 0.8 ± 0.7 |
| vs. Baseline | 17% better | 20% better |

TABLE 3i-continued

Non-significant changes in responses to CFQ

| Time | Group taking one capsule of beta-caryophyllene (BCP) daily (n = 26) | Group taking two capsules of beta-caryophyllene daily (n = 26) |
|---|---|---|
| Do you confuse left and right when giving people directions? | | |
| Baseline | 0.6 ± 1.0 | 0.9 ± 1.2 |
| Week 4 | 0.7 ± 1.0 | 0.7 ± 0.8 |
| vs. Baseline | 17% worse | 22% better |
| Week 8 | 0.7 ± 0.9 | 0.7 ± 0.8 |
| vs. Baseline | 17% worse | 22% better |
| Do you bump into people? | | |
| Baseline | 0.7 ± 0.6 | 0.7 ± 1.0 |
| Week 4 | 0.5 ± 0.6 | 0.6 ± 0.8 |
| vs. Baseline | 29% better | 14% better |
| Week 8 | 0.7 ± 0.6 | 0.5 ± 0.6 |
| vs. Baseline | No change | 29% better |
| Do you fail to listen to people's names when you are meeting them for the first time? | | |
| Baseline | 2.2 ± 1.0 | 2.3 ± 1.1 |
| Week 4 | 2.2 ± 1.1 | 1.8 ± 1.2 |
| vs. Baseline | No change | 22% better |
| Week 8 | 1.9 ± 1.2 | 1.9 ± 1.1 |
| vs. Baseline | 14% better | 17% better |
| Do you say something and realize afterwards that it might be taken as an insult? | | |
| Baseline | 1.5 ± 0.9 | 1.4 ± 0.8 |
| Week 4 | 1.1 ± 1.0 | 1.4 ± 0.9 |
| vs. Baseline | 28% better | No change |
| Week 8 | 1.2 ± 0.7 | 1.2 ± 0.7 |
| vs. Baseline | 20% better | 14% better |
| Do you fail to hear people speaking to you when you are doing something? | | |
| Baseline | 2.0 ± 0.8 | 1.7 ± 0.8 |
| Week 4 | 1.7 ± 0.9 | 1.5 ± 1.1 |
| vs. Baseline | 15% better | 12% better |
| Week 8 | 1.6 ± 0.9 | 1.3 ± 1.1 |
| vs. Baseline | 20% better | 23% better |
| Do you lose your temper and regret it? | | |
| Baseline | 1.1 ± 0.7 | 1.5 ± 0.9 |
| Week 4 | 1.1 ± 0.7 | 1.1 ± 0.8 |
| vs. Baseline | No change | 26% better |
| Week 8 | 1.0 ± 0.6 | 1.0 ± 0.7 |
| vs. Baseline | 9% better | 33% better |
| Do you fail to see what you want in a supermarket (although it's there)? | | |
| Baseline | 1.4 ± 0.9 | 1.3 ± 1.1 |
| Week 4 | 1.2 ± 0.7 | 1.1 ± 1.0 |
| vs. Baseline | 14% better | 15% better |
| Week 8 | 1.3 ± 0.9 | 1.0 ± 0.8 |
| vs. Baseline | 7% better | 23% better |
| Do you find yourself suddenly wondering if you used a word correctly? | | |
| Baseline | 1.4 ± 1.0 | 1.4 ± 1.2 |
| Week 4 | 1.2 ± 0.8 | 1.0 ± 1.1 |
| vs. Baseline | 14% better | 29% better |
| Week 8 | 1.2 ± 0.7 | 0.8 ± 0.9 |
| vs. Baseline | 14% better | 43% better |

TABLE 3i-continued

Non-significant changes in responses to CFQ

| Time | Group taking one capsule of beta-caryophyllene (BCP) daily (n = 26) | Group taking two capsules of beta-caryophyllene daily (n = 26) |
|---|---|---|
| Do you have trouble making up your mind? | | |
| Baseline | 1.5 ± 0.9 | 1.9 ± 1.2 |
| Week 4 | 1.3 ± 0.7 | 1.5 ± 1.1 |
| vs. Baseline | 13% better | 21% better |
| Week 8 | 1.4 ± 0.9 | 1.4 ± 0.9 |
| vs. Baseline | 7% better | 26% better |
| Do you find that you forget appointments? | | |
| Baseline | 0.8 ± 0.7 | 1.0 ± 1.0 |
| Week 4 | 1.0 ± 0.7 | 0.7 ± 0.8 |
| vs. Baseline | 25% worse | 30% better |
| Week 8 | 0.9 ± 0.8 | 0.5 ± 0.5 |
| vs. Baseline | 13% worse | 50% better |
| Do you find that you drop things? | | |
| Baseline | 1.4 ± 0.9 | 1.5 ± 0.9 |
| Week 4 | 1.2 ± 0.9 | 1.1 ± 0.7 |
| vs. Baseline | 14% better | 27% better |
| Week 8 | 1.2 ± 0.7 | 1.0 ± 0.7 |
| vs. Baseline | 14% better | 33% better |

TABLE 4

Cambridge Brain Sciences actual scores and percentage change over 8 weeks

| Test | Baseline | Week 4 | Week 8 |
|---|---|---|---|
| Taking one beta-caryophyllene (BCP) capsule | | | |
| Spatial Planning | 102 ± 11 | 104 ± 9 | +2.3% |
| Double Trouble | 88 ± 12 | 93 ± 15 | +5.3% |
| Monkey Ladder | 101 ± 6 | 103.8 ± 6.7 | +2.5% |
| Feature Match | 96 ± 6 | 98.3 ± 6.9 | +2.0% |
| Taking two beta-caryophyllene (BCP) capsules | | | |
| Spatial Planning | 96 ± 10 | 102.5 ± 7.8 * | +7% |
| Double Trouble | 88 ± 12 | 97.3 ± 15.2 * | +10% |
| Monkey Ladder | 102 ± 6 | 103.7 ± 8.1 | +2% |
| Feature Match | 99 ± 7 | 98.4 ± 7.6 | No change |

* $P \leq 0.05$ compared to baseline by t-test

TABLE 5

Improvement, worsening, and no change in Cambridge Brain Sciences tests between baseline and week 8

| | Spatial Planning | Double Trouble | Monkey Ladder | Feature Match |
|---|---|---|---|---|
| Taking one beta-caryophyllene (BCP) capsule | | | | |
| N | 26 | 25 | 23 | 24 |
| Improved | 19 (73%) | 15 (60%) | 16 (70%) | 13 (54%) |
| No change | 2 (8%) | 0 | 1 (4%) | 3 (13%) |
| Worsened | 5 (19%) | 9 (36%) | 6 (26%) | 8 (33%) |
| Taking two beta-caryophyllene (BCP) capsules | | | | |
| N | 25 | 22 | 25 | 25 |
| Improved | 18 (72%) | 14 (64%) | 17 (68%) | 10 (40%) |
| No change | 2 (8%) | 3 (14%) | 7 (28%) | 4 (16%) |
| Worsened | 5 (20%) | 5 (23%) | 1 (4%) | 11 (44%) |

TABLE 6

Summed means of the four Cambridge Brain Sciences test scores at baseline and week 8 (lower scores indicate worse cognitive function)

| Grouping of participants by dietary intervention and mean baseline score of the four tests | Mean of four tests scores at baseline | Mean of four tests scores at week 8 | Percentage change (mean ± S.D.) |
|---|---|---|---|
| Taking one beta-caryophyllene (BCP) capsule | | | |
| Mean of four tests | 96.8 | 99.8 | 3.6 ± 10.0 |
| Mean of four tests that were less than or equal to 100 | 92.3 | 96.8 | 5.0 ± 9.8 |
| Mean of four tests that were greater than 100 | 110.0 | 108.7 | −0.7 ± 9.4% |

TABLE 6-continued

Summed means of the four Cambridge Brain Sciences test scores at baseline and week 8 (lower scores indicate worse cognitive function)

| Grouping of participants by dietary intervention and mean baseline score of the four tests | Mean of four tests scores at baseline | Mean of four tests scores at week 8 | Percentage change (mean ± S.D.) |
|---|---|---|---|
| Taking two BCP capsules | | | |
| Mean of four tests | 97.2 | 101.0 | 4.6 ± 12.1 |
| Mean of four tests that were less than or equal to 100 | 91.0 | 98.8 | 9.0 ± 12.9 |
| Mean of four tests that were greater than 100 | 105.7 | 104.2 | −1.5 ± 7.5 |

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. A therapeutic method of treating mild cognitive impairment and improving human cognitive function, comprising: daily, for a period of a plurality of weeks, orally administering a dose of at least about 90 mg Beta-Caryophyllene (BCP) to a human subject, whereas the BCP improves cognitive function as measured by the human subject's responses to one or more standard questionnaires.

2. The method of claim 1, wherein the administration of a dose of at least about 90 mg BCP daily continued for up to eight weeks.

3. The method of claim 1, wherein the BCP is administered in a dose of at least about 180 mg daily.

4. The method of claim 1, wherein the BCP improves cognitive function by at least about 8%.

5. The method of claim 1, wherein the BCP improves cognitive function by up to about 63%.

6. The method of claim 1, wherein the BCP is delivered orally via a pre-measured and filled gelatin capsule.

7. The method of claim 6, wherein cognitive function was measured after four weeks and eight weeks of daily BCP administration.

8. The method of claim 7, wherein cognitive function improved by all measures after four weeks of daily BCP administration.

9. The method of claim 8, wherein cognitive function improved by all measures after eight weeks of daily BCP administration as compared to four weeks of daily BCP administration.

10. The method of claim 7, wherein cognitive function improvement over 8 weeks is about twice as great as that over 4 weeks.

11. The method of claim 10, wherein cognitive improvement after 4 weeks is about 5% and over 8 weeks is about 9%.

12. The method of claim 1, wherein the BCP is derived from at least one of oregano, cinnamon, clove, rosemary, wild sage, thyme, and black pepper.

13. The method of claim 1, wherein the BCP is delivered orally via at least one of a mint, chewing gum, a misting spray, a lozenge, and a chewable.

* * * * *